US00PP31156P2

(12) United States Plant Patent
Hansen

(10) Patent No.: US PP31,156 P2
(45) Date of Patent: Dec. 3, 2019

(54) ***EUCOMIS* PLANT NAMED 'SAFARI ADVENTURE'**

(50) Latin Name: *Eucomis comosa*
Varietal Denomination: Safari Adventure

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,797

(22) Filed: Jan. 14, 2019

(51) Int. Cl.
*A01H 5/02* (2018.01)
*A01H 6/12* (2018.01)

(52) U.S. Cl.
USPC ..... Plt./263.1

(58) Field of Classification Search
USPC ..... Plt./263.1
CPC ..... A01H 5/02; A01H 6/12
See application file for complete search history.

*Primary Examiner* — Annette H Para

(57) ABSTRACT

A new and distinct *Eucomis* plant named 'Safari Adventure' with rounded-mound habit of glossy, finely wavy, finely serrulate, strap-like, olive-green foliage emerging with wine-colored blushing. Beginning in mid-summer and lasting for about four weeks, the plants produce tall racemes with dense flowers that open creamy white from greyed purple buds and become deep rosy purple with maturity. 'Safari Adventure' is winter-hardy to USDA zone 6 and useful as a specimen landscape plant, en masse, as a container plant or as a cut flower.

1 Drawing Sheet

Latin name and variety denomination of the plant:
Botanical classification: *Eucomis comosa.*
Variety denomination: 'Safari Adventure'.

STATEMENT REGARDING PRIOR DISCLOSURES UNDER 37 CFR 1.77(B)(6)

The first public disclosure of the claimed plant was made by Walters Gardens, Inc. on Feb. 1, 2018 when the claimed plant was displayed as a photograph with short description on a website owned and operated by Walters Gardens, Inc., and the initial sales of the new plants was on Jul. 16, 2018, also by Walters Gardens, Inc. who obtained the plant and all information relating thereto, from the inventor. No plants of *Eucomis* 'Safari Adventure' have been sold, in this country or anywhere in the world, nor has any disclosure of the new plant been made, more than one year prior the filing date of this application, and such disclosure within one year was either derived directly or indirectly from the inventor.

BACKGROUND AND ORIGIN OF THE PLANT

There are twelve recognized species within the genus *Eucomis* in the Asparagaceae family. The present invention relates to a new and distinct hosta plant, *Eucomis* 'Safari Adventure' hereinafter also referred to as the new plant or the cultivar name, 'Safari Adventure'. *Eucomis* 'Safari Adventure' was hybridized by the inventor at a wholesale nursery in Zeeland, Mich., USA on Jul. 16, 2009 as a cross with *Eucomis comosa* 'Toffee' (not patented) as the female and the male parent is *Eucomis comosa* 'Sparkling Burgundy'. Seeds from this cross were planted on Sep. 21, 2009. The new plant is the selection of a single seedling among several in the cross identified by the breeder code H9-11-x through the trial process. The new plant has been asexually propagated initially by division of the bulbs and later by leaf accessions at the same nursery in Zeeland, Mich., USA since 2014, with the resultant asexually propagated plants having retained all the same traits as the original plant.

BRIEF SUMMARY OF THE PLANT

*Eucomis* 'Safari Adventure' is a distinct and new variety of Pineapple Lily.

The nearest comparison cultivar known to the inventor is 'Sparkling Burgundy' (not patented.) Compared with the new plant, 'Sparkling Burgundy' has deeper wine blushed foliage and the flowers are not as dramatic in changing from ivory white to deep rosy purple. 'African Night' U.S. Plant patent application Ser. No. 16/350,796 has rich burgundy foliage as emerging, and the flower color is rosy pink upon opening and stays rosy pink through maturity. The female parent has green foliage that emerges bronze and the flowers are white.

*Eucomis* 'Safari Adventure' is distinct from all cultivars known to the inventor in the following distinct traits:

1. Bulbous winter-hardy perennial with strap-shaped leaves emerging from the ground;
2. Foliage color begins emerging in the spring olive-green blushed with wine coloring;
3. Leaves are glossy above and below and the margins are finely serrulate and finely wavy (repand);
4. Each mature bulb produces a tall raceme with dense flowers that open creamy white from greyed-purple buds and develop to a deep rosy purple;
5. Winter-hardy to USDA zone 6.

BRIEF DESCRIPTION OF THE DRAWINGS

The photographs of the new plant demonstrate the overall appearance of the new plant, including the unique traits grown in full-sun trial gardens in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
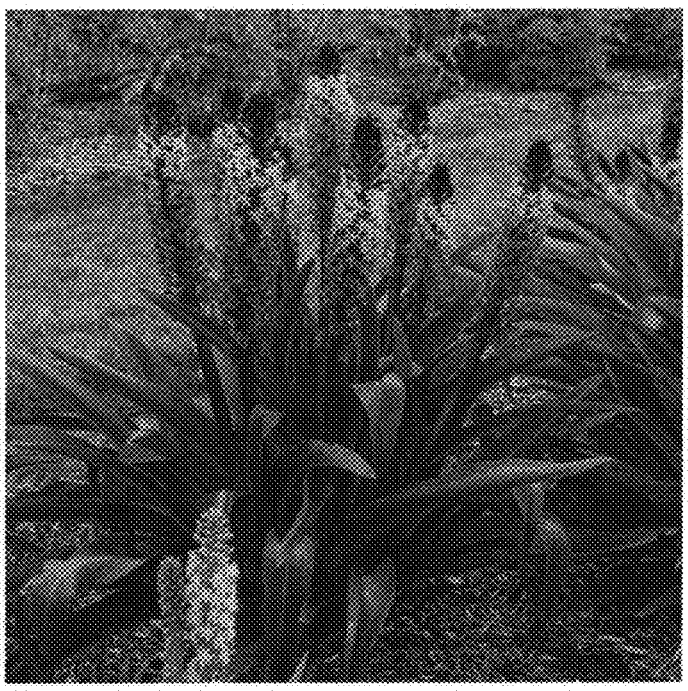
FIG. 1 shows the plant habit of an eight-year-old plant.
Figure 2:
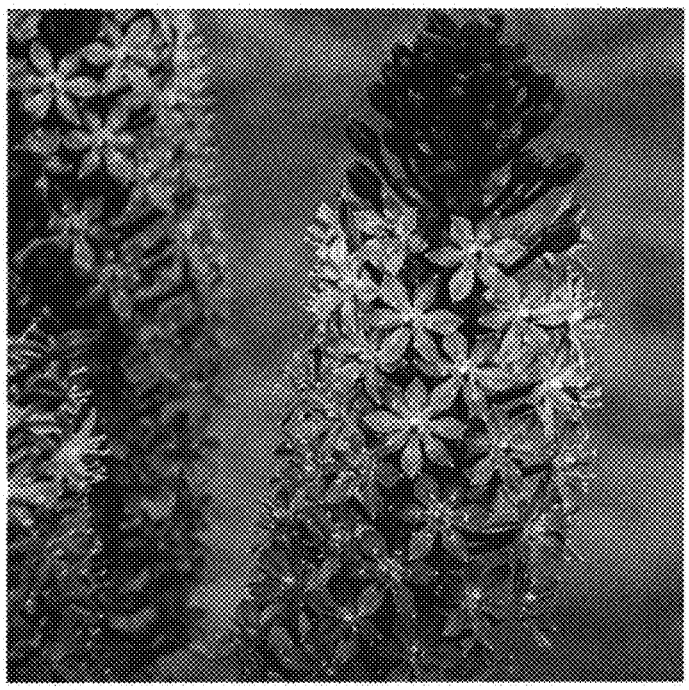
FIG. 2 shows a close-up of the flowering scape with dark buds and open flowers of changing colors.

The following descriptions and color references are based on the 2015 edition of The Royal Horticultural Society Colour Chart except where common dictionary terms are used. The new plant, *Eucomis* 'Safari Adventure', has not been observed under all possible environments. The phenotype may vary slightly with different environmental conditions, such as temperature, light, fertility, moisture and maturity levels, but without any change in the genotype. The following observations and size descriptions are of an eight-year-old plant in a full-sun trial garden in Zeeland, Mich. with supplemental water and fertilizer.

Botanical classification: *Eucomis comosa;*

Parentage: *Eucomis comosa* 'Toffee' as the female parent, and the male parent is *Eucomis comosa* 'Sparkling Burgundy';

Propagation: Separation of the bulbs and leaf accessions;

Time to initiate bulblets from leaf accessions: About three months during the winter growing season;

Growth rate: Moderate;

Crop time: About two growing season to produce flowering size bulbs from a 25 mm liner;

Rooting habit: Normal, fleshy, lightly branching; color between RHS NN155D and RHS 158A depending on soil type and root age;

Plant shape and habit: Hardy herbaceous perennial with basal rosette of leaves emerging from bulbs producing a more or less symmetrical, rounded-mound of leaves and upright racemes of compact flowers and topknot of small leaves;

Plant size: Foliage height about 66.0 cm above soil line to the top of the leaves and about 90.0 cm wide at the widest point slightly above the soil line;

Bulb: Turbinate; tunicate; about 5.6 cm diameter and 3.5 cm tall; color variable with portions nearest RHS NN155C and other portions between RHS 175A and RHS 175B;

Foliage description: Acaulescent arising from bulb; linear; glabrous, lustrous abaxial and adaxial; lance, with narrowly acute apex and truncate base; margin finely repand and finely serrulate; blades generally flat, without twisting;

Leaf blade size: To about 55.0 cm long, 6.5 cm wide near base; average about 48.5 cm long, 5.2 cm wide;

Leaf blade color: Early emerging adaxial nearest RHS 146B with strong blushing of nearest RHS 187B, emerging abaxial nearest RHS 146C with blushing of nearest RHS 187B; mature adaxial nearest RHS 137A with slight blushing of nearest RHS 187B, mature abaxial nearest RHS 146C with slight blushing of nearest RHS 187B;

Veins: Parallel, not discernable; with fleshy thick midrib;

Veins color: Adaxial midrib nearest RHS 146D; abaxial midrib nearest RHS 138C;

Topknot: With seven to ten small leaves at apex of raceme; about 2.5 cm tall and 3.0 cm wide; topknot leaves ovate with acute apex and truncate base, margin entire; cupped; average about 20.0 mm long and 8.0 mm wide;

Topknot leaf color: Adaxial and abaxial nearest RHS 187A with undertones of nearest RHS 146B;

Inflorescence: Raceme; flowers radially arranged, non-secund; flowering portion about 45.0 cm long and 10.0 cm wide; racemes effective with flowers beginning late July for about four weeks in Michigan landscape or about two to three weeks as a cut flower depending on storage conditions; about 150 flowers per raceme;

Buds one day prior to opening: Ellipsoidal with rounded apex and base; 14.0 mm long, with and about 8.0 mm diameter;

Bud color: Nearest RHS 187A;

Flowers: Perfect; single; regular; actinomorphic; whorl; persistent; attitude outwardly to slightly upright; about 32.0 mm wide and 14.0 mm long, decreasing distally; individually persist for about two weeks;

Flower fragrance: Faintly sweet;

Tepal: Six; fleshy; glabrous; margin entire; obtuse; acute apex and truncate base; approximately 13.0 mm long and about 8.0 mm wide toward apex;

Tepal color: Young flower adaxial nearest RHS NN155C with center midrib nearest RHS 145C, abaxial nearest RHS NN155C; mature flower adaxial between RHS 71A and RHS 71B, abaxial nearest RHS 71B;

Gynoecium: Single; tri-carpelled; 11.0 mm long; exserted;

*Style*.—Single; cylindrical; approximately 7.0 mm long, 1.0 mm diameter at base; color nearest N186C.

*Stigma*.—Flattened; about 0.5 mm across; color nearest RHS NN187D.

*Ovary*.—Superior; globose; about 4.0 mm long and 3.5 mm diameter; rounded apex and truncate base; color nearest RHS NN155B initially and developing strong blushing of nearest RHS 71A.

Androecium:

*Filaments*.—Typically six; adnate to inner corolla and connate in basal 3.0 mm; cylindrical distally and flattened at base; approximately 10.0 mm long and 3.0 mm wide at base; color upon initial anthesis nearest RHS 145C, maturing nearest RHS N186D.

*Anthers*.—Oblanceolate; dorsifixed, longitudinal; about 4.0 mm long and 2.0 mm wide; color nearest RHS 1A.

*Pollen*.—Abundant; elliptic, less than 0.1 mm long; color nearest RHS 4B.

Peduncle: Terete; usually one per mature division and eight per plant; lustrous, glabrous; upwardly; to about 88.0 cm tall, and about 30.0 mm in diameter at base; average about 84.0 cm and 28.0 mm diameter;

Peduncle color: When flowering nearest RHS N186C;

Pedicel: Glabrous; lustrous; cylindrical; slightly upwardly; approximately 30.0 mm long and 2.5 mm diameter;

Pedicel color: Nearest RHS N186C;

Foliar bract: Each flower subtended by a single bract, deltoid; acute apex; truncate clasping base; entire margin; about 6.0 mm long and 8.0 mm across base; color nearest RHS 146D with blushing of nearest RHS 187B;

Fruit: Ellipsoidal; with acute apex and truncate base; tri-valved dehiscent capsule; about 8.0 cm long and 8.0 mm across; color when mature nearest RHS 177A;

Seed: Globose; about 2.0 mm long and 1.5 mm wide; color nearest RHS 202A;

Disease tolerance and resistance: The new plant has not shown any resistance to pests and diseases common to Pineapple Lilies. The plant grows best and shows best coloration with plenty of moisture, adequate drainage and full sun. Winter hardiness has been tested in USDA zone 6. Other disease resistance is typical of that of other *Eucomis.*

It is claimed:

1. A new and distinct ornamental *Eucomis* cultivar named 'Safari Adventure' as herein described and illustrated.

* * * * *